United States Patent [19]

Chow et al.

[11] Patent Number: 4,959,219

[45] Date of Patent: Sep. 25, 1990

[54] COATING BARRIERS COMPRISING ETHYL CELLULOSE

[75] Inventors: San-Laung Chow; Yegnaswami Raghunathan, both of Perinton, N.Y.

[73] Assignee: Fisons Corporation, Rochester, N.Y.

[21] Appl. No.: 231,933

[22] Filed: Aug. 15, 1988

[51] Int. Cl.$^5$ .......................... A61K 9/36; A61K 9/62
[52] U.S. Cl. ...................................... 424/480; 424/79; 424/495; 424/498
[58] Field of Search ................... 424/480, 495, 498, 79

[56] References Cited

U.S. PATENT DOCUMENTS

| | | | |
|---|---|---|---|
| 2,881,085 | 4/1959 | Endicott et al. | 424/480 |
| 4,220,574 | 9/1980 | Perrone | 260/23.7 H |
| 4,221,778 | 9/1980 | Raghunathan | 424/31 |
| 4,521,401 | 6/1985 | Dunn | 424/480 |
| 4,693,896 | 9/1987 | Wheatley et al. | 424/480 |

FOREIGN PATENT DOCUMENTS

| | | | |
|---|---|---|---|
| 58-172311 | 10/1983 | Japan | 424/480 |
| 0899053 | 6/1962 | United Kingdom | 424/480 |

OTHER PUBLICATIONS

Kampouris et al, Actes Congr. Mond.-Soc. Int. Etude Corps Gras, 13th, 1976, Sym 6, pp. 5–14, Iterg: Paris, France.
CA 83: 148298n, 1975.
CA 97: 133590s, 1982.
Eastman Kodak, "Myvacet Distilled Acetylated Monoglycerides as Food Coatings", 1981 (4 pages).
Durkee, "USP/NF Corn Oil", 1984 (1 page).

Primary Examiner—Thurman K. Page
Attorney, Agent, or Firm—Seidel, Gonda, Lavorgna & Monaco

[57] ABSTRACT

Coatings for individual ion exchange resin particles comprised of (a) ethylcellulose and (b) corn oil or acetylated monoglycerides.

19 Claims, No Drawings

COATING BARRIERS COMPRISING ETHYL CELLULOSE

BACKGROUND OF THE INVENTION

This invention relates generally to coatings and more specifically to improved extended release coating barriers comprising a film-forming polymer and a plasticizer which are applicable to drug-resin complex particles.

U.S. Pat. No. 4,221,778, the specification of which is incorporated herein by reference, describes extended release pharmaceutical compositions with which the improved coatings of this invention are applicable, namely compositions comprised of individually coated drug-resin complex particles. The examples use a coating comprised of ethylcellulose and, as a plasticizer, Durkex ® 500 (partially hydrogenated cottonseed and soybean oils). It has been found, however, that the Durkex 500 has a tendency to form a cloudy precipitate when stored or shipped below about 23° C.

BRIEF SUMMARY OF THE INVENTION

The present invention is concerned with coatings for individual ion exchange resin particles comprised of (a) ethylcellulose and (b) corn oil or acetylated monoglycerides (AMG) with congealing temperatures below about 23° C. It is also concerned with improved, extended release pharmaceutical compositions comprised of individually coated drug-resin complex particles, the improvement consisting of the use of the aforedescribed coatings. As in U.S. Pat. No. 4,221,778, it is preferred that the particles be treated, prior to coating, with a solvating agent such as polyethylene glycol, the resulting coated particles providing a highly efficient extended release of drug under conditions such as those encountered in the gastrointestinal tract.

DETAILED DESCRIPTION OF THE INVENTION

It has now been found that corn oil (congealing points of about −18° to −10° C.) or AMG (congealing point of about 8° C.) render a highly efficient extended release coating barrier when used with ethylcellulose, as well as staying clear during shipment and storage.

A practical range of use for either AMG or corn oil is from about 1.6 to about 8% by weight, based on the weight of the coated particles, with preferred ranges being about 4.6 to 6.9% (most preferably 4.8–5.6%) for corn oil and 1.6 to 2.4% for AMG. The examples below show that coatings made with these materials may be used to prolong the release of drugs from drug-resin complex particles. Conventional coating solvents (such as ethanol, or a methylene chloride/acetone mixture, or coating emulsions) and coating procedures (such as fluid bed coating) can be employed to coat the particles. Techniques of fluid bed coating are taught, for example, in U.S. Pat. Nos. 3,089,824; 3,117,027 and 3,253,944. When preparing a coated drug resin complex, the coating is applied to the drug resin complex. In the examples to follow (except as otherwise stated) pretreated drug-resin complex particles are coated at a constant level of 16% by weight as combined weights of the ethylcellulose and plasticizer in the coated particles. The coating solution is prepared by dissolving the plasticizer and ethylcellulose in acetone and methylene chloride. The coating of the drug-resin complex particles is carried out in a suitable, 4/6-inch fluid bed coating apparatus at a rate of 16-17 ml of coating solution per minute. The inlet air temperature is about 33° C. and the outlet air temperature is about 22°–25° C. The atomizing air pressure is 30 psi and the fluidized air pressure is adjusted as required.

In general when preparing coated drug-resin complex particles, all pharmacologically active basic drugs, especially those having short biological half-lives in the order of up to about 8 hours, are potential candidates for inclusion in the subject preparations. Examples include, but are not limited to, codeine, dextromethorphan, doxepin, ephedrine, hydrocodone, hydralazine, metaproterenol, morphine, phenylpropanolamine, pseudoephedrine, and verapamil. Phenylpropanolamine (PPA), a sympathomimetic amine drug with a biological half life of 3.9 hours in man and a pKa of 9.4, was chosen as a model drug for use in illustrative examples 1-11. The resin is a sulfonic acid cationic exchange resin, normally in particle sizes ranging from about 25 to about 1000 $\mu$m. The illustrative examples employ Amberlite ® IRP-70 resin, a cationic exchange resin which is 100–200 mesh (75–150 $\mu$m) fractured resin particles of Amberlite IR-120. The parent resin of Amberlite IR-120 and Amberlite IRP-70 is described by the manufacturer as a gel-type divinylbenzene sulfonic acid cationic exchange resin which swells in water with a pH range of 0-14. The resin should not have inherent pharmacological or toxic properties.

Adsorption of the drug onto the ion exchange resin particles to form the drug resin complex is a well known technique as shown in U.S. Pat. Nos. 2,990,332 and 4,221,778. In general the drug is mixed with an aqueous suspension of the resin, and the complex is then washed and dried. Adsorption of drug onto the resin may be detected by a change in the pH of the reaction medium.

Pretreatment of the drug-resin particles with an aqueous solution of a solvating agent such as polyethylene glycol (for example, PEG 3350) is known as disclosed in U.S. Pat. No. 4,221,778.

As shown in the experimental section below, an untreated and uncoated drug-resin complex (Control) rapidly releases its drug (86.5% in 30 minutes) in a simulated gastric fluid (0.1 normal hydrochloric acid). Uncoated, but polyethylene glycol treated, drug resin complex particles (Comparative Example) show essentially no prolongation in drug release either (82.1% release of drug in 30 minutes). However, the release rate is drastically retarded (15.7–33.9% release in 30 minutes) when the polyethylene glycol pretreated drug-resin complex particles are coated with coating barriers containing either corn oil or acetylated monoglycerides (Examples 1–11).

Variation in the amount of coating and/or the use of coated/uncoated complex mixtures can be employed to selectively modify the dissolution profile as desired. In addition to the application to a pretreated drug-resin complex system, the subject invention is also applicable to powder, crystal, granule, nonpareil seed, pellet, tablet and untreated drug-resin complex systems (see, e.g., Examples 12 and 13).

The following dissolution test apparatus and procedures are used in Examples 1-11 to simulate conditions encountered in the gastrointestinal tract: Five hundred ml of the dissolution medium (0.1N HCl) is placed in a round bottom flask immersed in a suitable water bath and the temperature allowed to rise to 37°±0.5° C. The flask is equipped with a paddle which is agitated at 100 rpm. The dissolution medium is pumped from the vessel through a cotton filter. Polyethylene tubing carries the filtered media via a peristaltic pump through a 1 cm flow cell of a Beckman model 35 recording spectrophotometer (equipped with a cell changer) and returns it to the vessel. The flow rate is adjusted to 16 ml/minute. In this way, each of six vessels and a standard can be monitored at 15 minutes or other suitable intervals. The spectrophotometer is operated at 257 nm in a single beam mode to monitor six resin complex samples and one PPA hydrochloride standard. Each dissolution vessel contains resin complex sample equivalent to 90.6 mg of PPA base. The standard PPA solution contains 90.6 mg of PPA based in 500 ml of 0.1N HCl. The drug released is then expressed as a percentage of the total drug present in the complex particles. The methods were suitably modified for Examples 12–13.

EXPERIMENTAL SECTION

Control-Uncoated and Untreated PPA Resin-Complex:

A large batch of PPA resin-complex was prepared as a control. The PPA hydrochloride (97 kg) was dissolved with stirring in 850 liters of deionized water in a glass lined mixing kettle. The Amberlite IRP-70 resin (244 kg), washed hydrogen cycle, was then added to the stirring PPA hydrochloride solution. The mixing was continued for 2 hours. The resin slurry was then transferred to the holding tank and then to the centrifuge. The resin core was washed with deionized water for at least 10 minutes until free of chloride ions. The resin core was then dried to a moisture of about 5% in a fluid bed dryer at 70° C. inlet air temperature. The dried resin complex was found to contain 23.8% of PPA. Dissolution results are shown in Table I.

COMPARATIVE EXAMPLE

Uncoated and PEG-Treated PPA Resin-Complex:

A typical batch of PEG-treated PPA resin complex was prepared as follows, from a formulation of deionized water (1.6 kg), PEG 3350 (1.0 kg), and PPA polistirex (4.0 kg):

The PEG 3350 was dissolved in the deionized water and added slowly to a mixer containing PPA polistirex. After mixing for 10 minutes, the PEG-treated PPA polistirex was transferred to a fluid bed dryer and dried at 50° C. Dissolution results on PEG-treated PPA resin complex particles are shown in Table I.

EXAMPLES 1 TO 5

Coated PEG Pretreated PPA Resin-Complex Using Corn Oil

Two lots each of PEG pretreated PPA resin-complex particles were coated using corn oil as plasticizer at the levels of 2.4, 4.0, 4.8, 5.6 and 8.0% (w/w) based on the total weight of coated particles. At 8%, however, the coated particles show a tendency to agglomerate when placed in the dissolution medium. The dissolution results are shown in Table I.

EXAMPLES 6 TO 11

Coated PEG Pretreated PPA Resin-Complex Using AMG

Two lots each of PEG pretreated PPA resin-complex particles were coated, using acetylated monoglycerides as plasticizer, at the levels of 1.6, 2.4, 4.0, 4.8, 5.6 and 8.0% based on the total weight of coated particles. At 8% the coated particles show a tendency to agglomerate when placed in a dissolution medium. The results are shown in Table I.

TABLE I

Release Profiles of PPA from PPA Resin-Complex Under Different Conditions

| Conditions | % PPA Release at | | |
|---|---|---|---|
| | 0.5 hour | 1.0 hour | 3.0 hours |
| Control | 86.5 | 86.4 | 93.0 |
| Comparative Example | 82.1 | 82.7 | 83.8 |
| Example 1, Corn oil 2.4% | 25.5 | 33.1 | 50.1 |
| Example 2, Corn oil 4.0% | 22.9 | 31.3 | 47.5 |
| Example 3, Corn oil 4.8% | 16.1 | 20.7 | 40.0 |
| Example 4, Corn oil 5.6% | 15.8 | 20.8 | 33.2 |
| Example 5, Corn oil 8.0% | 33.9 | 42.3 | 58.5 |
| Example 6, AMG 1.6% | 15.7 | 18.4 | 29.3 |
| Example 7, AMG 2.4% | 17.3 | 21.9 | 37.1 |
| Example 8, AMG 4.0% | 20.1 | 28.3 | 42.7 |
| Example 9, AMG 4.8% | 22.9 | 27.1 | 38.6 |
| Example 10, AMG 5.6% | 19.6 | 24.8 | 40.0 |
| Example 11, AMG 8.0% | 20.3 | 28.0 | 46.4 |

EXAMPLES 12 AND 13

Extended Release Tablets:

Using the same techniques as set forth above, coated pseudoephedrine polistirex was made by coating a PEG-treated pseudoephedrine polistirex at 18% weight/weight using a coating solution containing ethylcellulose (50 cps) and AMG at a ratio of 9:1 and, similarly, coated hydrocodone polistirex was made by treating a PEG-treated hydrocodone polistirex at 10.7% (w/w) with the same coating solution. These coated drug-resinate particles were then in turn used to prepare tablets as follows:

| A. Pseudoephedrine Extended Release Tablet - Example 12 | |
|---|---|
| 1. Formula: | mg/tablet |
| Coated pseudoephedrine polistirex | 260.6* |
| Carboxypolymethylene | 3.5 |
| Colloidal silicon dioxide | 0.9 |
| Magnesium stearate | 2.0 |
| Microcrystalline cellulose, coarse qs | 500.0 |

*Based on an assay of 18.86% pseudoephedrine base. The total amount of coated pseudoephedrine polistirex is equivalent to 60 mg pseudoephedrine hydrochloride or 49.15 mg pseudoephedrine base.

2. Procedure:
a. Mix carboxypolymethylene and colloidal silicon dioxide with microcrystalline cellulose and pass through #20 mesh stainless steel screen.
b. Mix coated pseudoephedrine polistirex with the remaining microcrystalline cellulose.
c. Mix powders from Step a and b.
d. Pass magnesium stearate through #30 mesh stainless steel screen and mix with the batch from c.
e. Compress the batch into tablets having a weight of about 500 mg, a 7/16 inch diameter, and thicknesses ranging from 0.231 to 0.269 inches.

3. Results:
The tablets consistently show extended release profiles.

| B. Hydrocodone with Chlorpheniramine Extended Release Tablet - Example 13 | |
|---|---|
| 1. Formula: | mg/tablet |
| Coated hydrocodone polistirex | 56.0* |
| Chlorpheniramine polistirex | 22.7* |
| Carboxypolymethylene | 3.2 |
| Colloidal silicon dioxide | 0.8 |

-continued

| B. Hydrocodone with Chlorpheniramine Extended Release Tablet - Example 13 | |
|---|---|
| 1. Formula: | mg/tablet |
| Magnesium stearate | 1.8 |
| Microcrystalline cellulose, coarse qs | 300.0 |

*Amounts will vary slightly depending upon assay of coated hydrocodone polistirex and chlorpheniramine polistirex. The total of the coated hydrocodone polistirex is equivalent to 10 mg hydrocodone bitartrate (6.054 mg hydrocodone base) per tablet. The total of the chlorpheniramine polistirex is equivalent to 8 mg of chlorpheniramine maleate (5.624 mg chlorpheniramine base) per tablet.

2. The following procedure is used to prepare a typical batch size of 9.0 kg of hydrocodone with chlorpheniramine extended release tablets:
   a. Add the carboxypolymethylene and colloidal silicon dioxide to about 100 gm of the microcrystalline cellulose and mix.
   b. Pass this premix (Step a) through a suitable granulator equipped with a No. 30 mesh stainless steel screen.
   c. Blend the coated hydrocodone polistirex, the remainder of the microcrystalline cellulose and the premix from Step b.
   d. Pass the magnesium stearate through No. 30 mesh stainless steel screen and mix with the above mix from Step c.
   e. Divide the mix into two equal parts; part I and part II. Compress part I mix into soft tablets at a tablet weight of 300 mg and a tablet thickness of 0.135 inches. Compress Part II mix into hard tablets at a tablet weight of 300 mg and a tablet thickness of 0.120 inches. All tablets were trapezoid shaped with approximately 0.146 square inches area for each of the two surfaces.

3. Results:
Tablets from parts I and II each show extended release profiles for the hydrocodone.

What is claimed is:

1. An extended-release pharmaceutical composition comprised of individually coated phenylpropanolaminedivinylbenzene sulfonic acid cationic exchange resin particles, the improvement wherein the coating is comprised of (a) ethyl cellulose and (b) from about 1.6% to about 8% by weight corn oil or acetylated monoglycerides with congealing temperatures below about 23° C., based upon the weight of the coated particles.

2. In an extended release pharmaceutical composition comprised of individually coated drug-resin complex particles, the improvement wherein the coating is comprised of (a) ethylcellulose and (b) corn oil or acetylated monoglycerides with congealing temperatures below about 23° C.

3. The composition of claim 2 in tablet form.

4. The composition of claim 2 wherein the resin of the drug-resin complex particles comprises an ion-exchange resin.

5. The composition of claim 4 wherein component (b) of the coating comprises corn oil.

6. The composition of claim 4 wherein component (b) of the coating comprises acetylated monoglycerides with congealing temperatures below about 23° C.

7. The composition of claim 5 wherein the ion-exchange resin comprises a divinylbenzene sulfonic acid cationic exchange resin.

8. The composition of claim 6 wherein the ion-exchange resin comprises a divinylbenzene sulfonic acid cationic exchange resin.

9. The composition of claim 5 wherein the coated particles comprise from about 1.6% to about 8% by weight corn oil, based on the weight of the coated particles.

10. The composition of claim 6 wherein the coated particles comprise from about 1.6% to about 8% by weight acetylated monoglycerides with congealing temperatures below about 23° C., based on the weight of the coated particles.

11. The composition of claim 9 wherein the coated particles comprise from about 4.6% to about 6.9% by weight corn oil, based on the weight of the coated particles.

12. The composition of claim 9 wherein the coated particles comprise from about 1.6% to about 2.4% by weight acetylated monoglycerides with congealing temperatures below about 23° C., based on the weight of the coated particles.

13. The composition of claim 5 wherein the drug comprises phenylpropanolamine.

14. The composition of claim 6 wherein the drug comprises phenylpropanolamine.

15. The composition of claim 3 wherein the drug is selected from the group consisting of pseudoephedrine, hydrocodone, chlorpheniramine, and combinations thereof.

16. The composition of claim 15 wherein the drug comprises pseudoephedrine.

17. The composition of claim 15 wherein the drug comprises a mixture of hydrocodone and chlorpheniramine.

18. The composition of claim 1 containing from about 4.6% to about 6.9% by weight corn oil, based on the weight of the coated particles.

19. The composition of claim 1 containing from about 1.6% to about 2.4% by weight acetylated monoglycerides with congealing temperatures below about 23° C., based on the weight of the coated particles.

* * * * *